United States Patent [19]

Millis et al.

[11] Patent Number: 4,857,750

[45] Date of Patent: Aug. 15, 1989

[54] SENSOR FOR DETERMINING PHOTORESIST DEVELOPER STRENGTH

[75] Inventors: Edwin G. Millis, Dallas; Samuel J. Wood, Jr., Plano, both of Tex.

[73] Assignee: Texas Instruments Incorporated, Dallas, Tex.

[21] Appl. No.: 134,438

[22] Filed: Dec. 17, 1987

[51] Int. Cl.⁴ .......................... G01N 15/06; G01J 1/42
[52] U.S. Cl. ................................. 250/573; 250/373; 356/442; 354/298
[58] Field of Search ................ 354/298; 356/442, 440, 356/246; 355/10; 250/576, 574, 573, 373; 137/93; 437/229

[56] References Cited

U.S. PATENT DOCUMENTS

| | | | |
|---|---|---|---|
| 3,712,203 | 1/1973 | Kishi et al. | 354/298 |
| 3,722,559 | 3/1973 | Hoffman | 354/298 |
| 3,990,088 | 11/1976 | Takita | 354/298 |
| 4,021,832 | 5/1977 | Krehbiel et al. | 354/298 |
| 4,166,702 | 9/1979 | Okamoto et al. | 354/298 |
| 4,469,424 | 9/1984 | Matsui et al. | 354/298 |
| 4,669,847 | 6/1987 | Taniguchi et al. | 354/298 |
| 4,671,309 | 6/1987 | Iemura et al. | 137/93 |
| 4,796,590 | 1/1989 | Degobert et al. | 250/373 |

*Primary Examiner*—Davis C. Nelms
*Assistant Examiner*—Michael Messinger
*Attorney, Agent, or Firm*—Gary C. Honeycutt; Melvin Sharp; Rhys Merrett

[57] ABSTRACT

An optical analyzer and a developer recirculation system is used to determine the amount of photoresist polymer dissolved in a quantity of developer solution and the sensor output signal is utilized by a control computer to control the admission of fresh developer solution to replace used developer and maintain a fixed level of dissolved photoresist polymer to keep the developer bath at a fixed level of chemical activity.

8 Claims, 2 Drawing Sheets

SENSOR FOR DETERMINING PHOTORESIST DEVELOPER STRENGTH

FIELD OF THE INVENTION

This invention relates to photoresist development and more particularly to a sensor and system for maintaining the strength of a photoresist developer recirculating solution during development.

BACKGROUND OF THE INVENTION

Resist patterning techniques employed in the semiconductor lithographic process fundamental to integrated circuit manufacturing usually rely on a fluid dissolution step to remove photoresist polymer either made more soluble or left less resistant to dissolution by selective exposure to some type of photon irradiation or particle bombardment.

It is critically important to control this pattern developing dissolution carefully to achieve close dimensional control of pattern features, the tolerances of which affect yield and practicable design performance limits of semiconductor devices.

Resist develop processes attempt to hold substrate, resist, and exposing and developing system parameters fixed at optimum values in order to more predictably relate pattern dimensions to develop time employed.

In certain photoresist processes the importance of high precision temperature control of the developer and avoidance of the problems and difficulties of achieving uniform and reproducible distribution of develop solution by various spray techniques have motivated equipment and process designs employing recirculating developer solutions and provisions for complete immersion of the pattern surface of the semiconductor wafer. Such a method and design is disclosed in Pat. application Ser. No. 134,284, filed Dec. 17, 1987, and entitled "IN-LINE SINGLE SLICE IMMERSION DEVELOPMENT PROCESS AND MACHINE".

In any such process employing recirculating developer solution, monitoring and control of the chemical reactivity of the recirculating solution is of critical importance.

Polymers employed in the formulation of photoresists typically exhibit high optical transmission at visible and nearultraviolet wavelengths and sharply lower transmission for shorter wavelengths, whereas developer fluids exhibit high transmission throughout the spectrum. At very short wavelengths, optical transmission of the developer is reduced greatly by even very small proportions of dissolved photoresist polymer. At intermediate wavelengths, greater proportions of dissolved polymer are required to cause sufficient absorption to greatly reduce optical transmission, such that sensitivity of the technique may be substantially affected by the wavelength chosen.

As photoresist developer chemical reactivity is expended by the desired chemical reaction with exposed photoresist, dissolved photoresist polymer content of the developer solution increases and may be readily and continually monitored by ultraviolet light transmission analysis. Such a method is disclosed in U.S. patent application Ser. No. 134,439, filed Dec. 17, 1987 and entitled "PROCESS AND SYSTEM FOR DETERMINING PHOTORESIST DEVELOP ENDPOINT BY EFFLUENT ANALYSIS". Thus, remaining chemical reactivity of the recirculated developer may be known by relation to polymer content, and solution dump and replenishment valves automatically controlled to maintain a preselected level of developer effectiveness.

SUMMARY OF THE INVENTION

This invention is an optical sensor system in which the sensor is used to monitor and control chemical reactivity of the developer solution used in an immersion developer bath for developing photoresist patterns on semiconductor wafers. In practice, the sensor may be used to monitor any solution in which the optical transmission is changed as the solution optical properties change during the processing.

The sensor is designed such that the developer solution flows through a part of the sensor housing. The optical transmission path, in which the developer flows, is about 3 centimeters in length. A light wavelength of about 254 nanometers (nm) is used. This wavelength corresponds to the part of the light spectrum that is strongly absorbed by dissolved photoresist in the developer.

The sensor includes a light source that produces light in the 254 nm wavelength region and is on one end of the sensor housing. The light transmitted through the developer solution is passed through a focusing lens and a 254 nm filter and impinges on a photo detector. The output of the detector is transmitted to an analyzer which, based on the amount of 254 nm light received by the detector, determines the chemical activity of the developer solution.

The system in which the sensor is used establishes a reference based on the optical transmission of the fresh or unused developer. As semiconductor wafers are processed in the developer, the chemical activity of the developer is monitored and fresh developer is automatically added as necessary to maintain the developer chemical activity at a predetermined level.

Provisions are included in the present invention to frequently recalibrate the optical analyzer system with regard to: illuminator and filter actinic output; spectral sensitivity of the photodetector; photodetector amplifier gain; analog-to-digital conversion; and minor accumulation on wetted surfaces of the lamp and lens of material deposited from the solution. Changes in any of the foregoing would introduce error into the optical transmission analysis if not canceled or compensated.

Calibration is accomplished by reference to the high optical transmission at 254 nm wavelength of fresh developer solution. This is accomplished on a frequent basis by means of a computer-controlled valve arrangement such that only the fresh developer solution being added in predetermined doses or increments, as commanded by a control computer, is briefly passed through the optical analysis cell.

After sufficient duration of a refortification dose for the optical transmission measurement to stabilize, the valve arrangement is reset by the control computer for reversion to monitoring a partial flow of the main volume of recirculating solution.

In order to make the optical analysis cell quickly responsive to small flows of solution, the fluid portion of the analyzer is a narrow configuration to minimize volume and maximize optical path length. In the recirculation monitoring valve arrangement, a relatively small bypass portion of the substantial recirculation flow is passed through the optical analysis cell.

A further advantage of an automatic recalibration capability may be realized when alternate developer systems which may have different optical absorption characteristics are used in the same recirculation developer system.

This invention and its features for monitoring and controlling chemical reactivity or concentration of critical solution constituents which may be detected by optical transmission have potential applications in other processes and systems employing recirculating chemical solutions such as those for; chemical etching or cleaning where increased dissolved inorganic or organic material may be detected; plating of metals; sedimentation coating; and liquid phase epitaxy. Other wavelengths for the illuminator and detector may be chosen as appropriate for specific case. Multiple wavelength analysis may be used. Fluorescent phenomena my be beneficially employed where detector spectral response is at a selected longer wavelength or wavelengths than that of the illuminator to enhance discrimination of process constituents.

The technical advance represented by the invention as well as the objects thereof will become apparent from the following description of a preferred embodiment of the invention when considered in conjunction with the accompanying drawings, and the novel features set forth in the appended claims.

DESCRIPTION OF A PREFERRED EMBODIMENT

Figure 1:
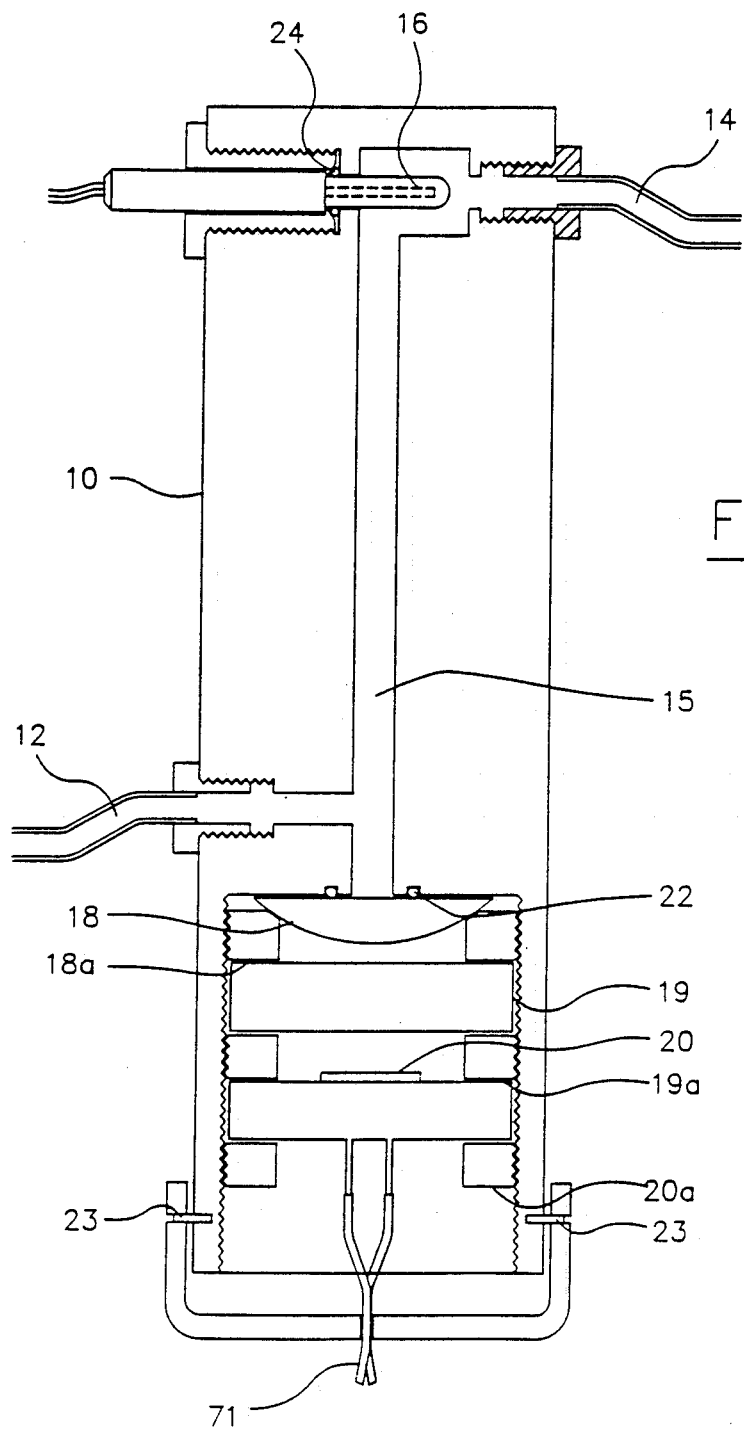
FIG. 1 illustrates a photo analysis cell of the present invention.

FIG. 1 illustrates a sensor of the present invention. The sensor has a housing 10 adapted to permit the flow of developer fluid or other chemical whose optical properties are to be measured. The developer is introduced into the body of the sensor at the input 12, and flows into the sensor housing into a fluid chamber 15, and out at the output port 14.

A low-pressure mercury-argon lamp 16 is mounted at one end of the housing 10 through an opening that is sealed by the lamp and an O-ring 24. On the end of the sensor housing opposite the lamp end is a photodetector 20. The detector may be optimally sensitive in the 254 nm wavelength range. The fluid chamber is sealed from the detector by a quartz lens 18 and an O-ring 22. The lens is used to focus the light from the lamp on to the photodetector. A 254 nm wave length dielectric interference filter 19 is used to filter the light from the lamp to pass light of only the 254 nm wavelength. The lens 18, filter 19 and photodetector are held in place by ring nuts 18a, 19a and 20a respectively. The detector, filter and lens is assessed by removing end cap 22, which is held to the housing 10 by pins 23. The output of the detector depends upon the amount of photoresist polymer dissolved in the developer that is flowing through the sensor.

Figure 2:
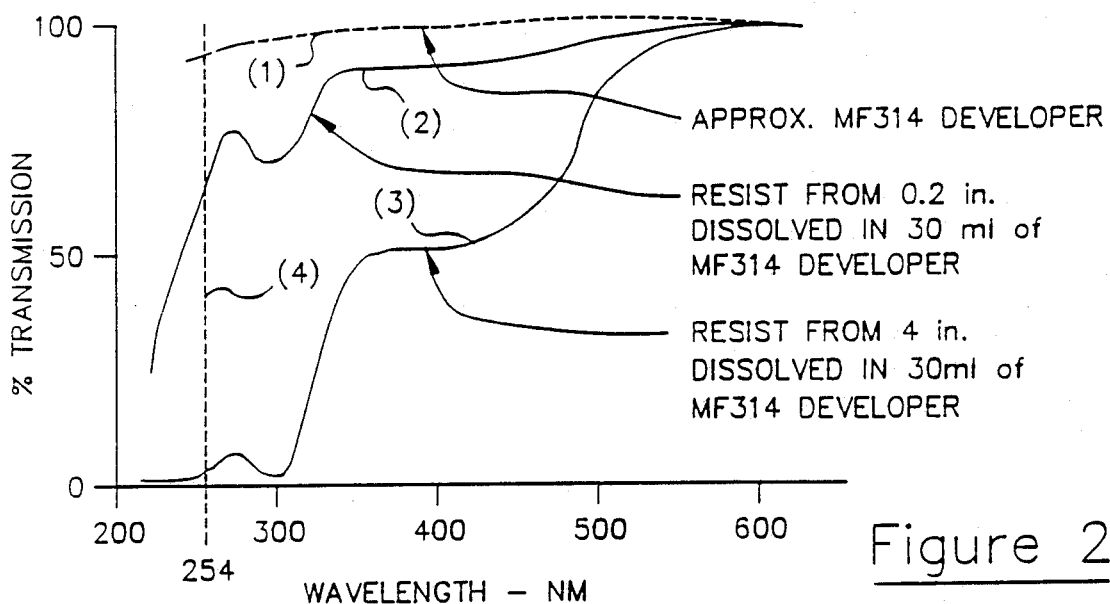
FIG. 2 is a graph illustrating the optical properties of a developer fluid with various amounts of photoresist polymer dissolved therein.

The relationship between the transmission properties of the polymer-laden developer and the wavelength of the light impinging on the detector is illustrated in FIG. 2.

FIG. 2 illustrates the optical properties of a photoresist developer, for example, the developer manufactured by Shipley Corp. and designated MF314. The graph in FIG. 2 is a comparison of the wavelength of light (x-axis) plotted against the percent of light transmission (y-axis) of the developer at different light wavelengths for; (1) the pure developer, (2) an amount of photoresist polymer from a 0.2 sq. in. layer dissolved in 30 ml of MF314 developer, and (3) an amount of photoresist polymer from a 4 sq. in. layer dissolved in 30 ml of MF314 developer. Also illustrated is a vertical line (4) representative of a 254 nm beam of light. These curves indicate that there is a correlation between the amount of dissolved polymer in the developer and light transmission in the vicinity of 254 nm. The three curves also show a correlation in the transmission properties of the developer based on a particular wavelength of light, and the amount of polymer dissolved in the developer. For example, it may be seen that the percent of transmission reduces from about 50% when 20 ml of developer has resist dissolved in it from a 0.2 sq. in. area to nearly 0% when 30 ml of developer has resist dissolved from a 4 sq. in. area.

Figure 3:
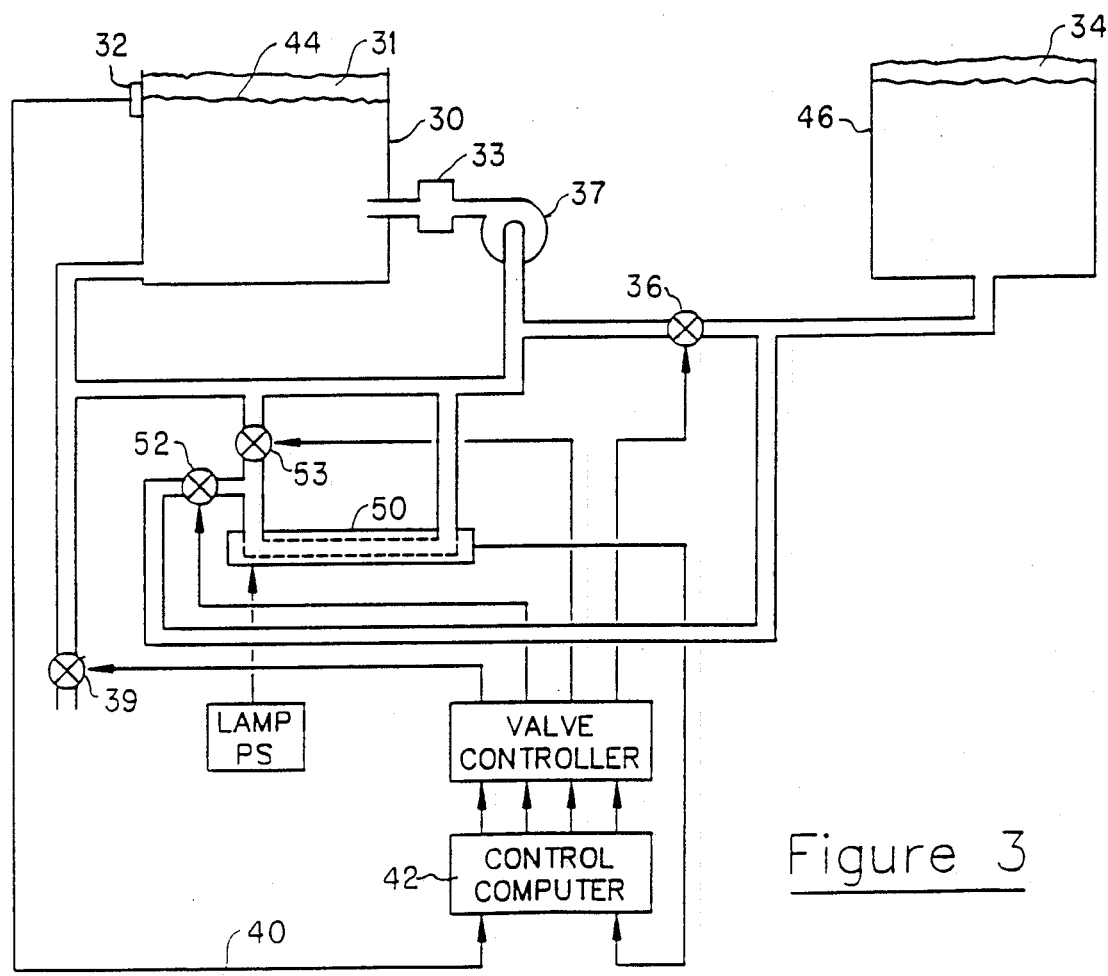
FIG. 3 illustrates a system for developing photoresist polymer patterns on a semiconductor wafer and for monitoring and replenishing developer in the system.

A system for developing photoresist patterns on a semiconductor wafer and a method of replenishing the developer bath is illustrated in FIG. 3. The system has a tank 30 for immersion of a semiconductor wafer on which photoresist is to be developed. The tank is filled with developer 44 to a level determined by level detector 32. A blanket of nitrogen 31 covers the tank to limit developer degradation from air. A replenisher tank 46 is filled with fresh developer and this developer is also covered with a blanket of nitrogen 34 introduced through inlet 35. The replenisher tank is connected to the immersion tank 30 by a valve 36, circulating pump 37 and a filter 33.

Connected between outlet 47 of the immersion tank and the circulating pump 37 is the optical sensor 50 of the present invention. The sensor is connected to a control computer 42.

The control computer 42 is interconnected with the detector output of the optical sensor, control valves 36, 39, 52 and 53, and the level sensor 32.

Operation of the system is as follows. A semiconductor wafer is lowered into the developer immersion tank to develop the patterned photoresist polymer on the wafer. As the developing progresses, photoresist polymer is dissolved into the developer fluid. Developer fluid is circulated out tank outlet 47, through optical sensor 38 and is returned to the through filter 33 by the circulating pump 37.

The photo sensor monitors the optical transparency of the developer fluid, such transparency being dependent upon the amount of photoresist dissolved in the developer fluid, and the signals out of the photo sensor are transmitted to the control computer by line 40. The control computer compares the optical transparency of the fluid with a known or measured value and reduces the percent of photoresist in the developer by opening control valve 36 to allow fresh developer fluid to be pumped into immersion tank 30. The control computer also monitors the level of developer in tank 30 via level sensor 32 and removes excess developer solution via dump valve 39.

In some processes, the sensor may be used to control the dumping of the entire solution when it becomes sufficiently saturated with photoresist rather than operating to control the developer strength. By continuous monitoring of the various parameters, the control computer maintains the developer fluid so as to produce a fixed development rate for the photoresist on the immersed semiconductor wafers.

For standardization of the analysis cell and related electronics during a limited portion of each recharge cycle, valves 36 and 53 are closed and valve 52 is opened until analysis cell-measured transmission stabilizes at a high value.

Valve 39 is continually controlled by the process vessel level sensor 32 and computer 42. All valve opening and closing is accomplished upon instructions from control computer 42. A lamp power supply is provided for the lamp in the analysis cell.

What is claimed is:

1. A system for analyzing the strength of a developer fluid and replenishing the developer fluid to maintain its strength comprising; an immersion tank into which an object having a layer of material to be developed is placed, an inlet and outlet to said immersion tank, means for recirculating the fluid from said outlet back to said inlet, a liquid analyser for analyzing the developer in said immersion tank comprising a mercury-argon lamp immersed in said fluid recirculating between said outlet and inlet of said immersion tank, a first valve for introducing fresh developer into said immersion tank, based on the results of analyzing said developer in said analyzer, and a second valve for removing developer from said tank.

2. The system according to claim 1, including a control computer for actuating said first and second valves based on the analysis of said developer in the liquid analyzer.

3. The system according to claim 1, including a level indicator and a replenishing tank, said level indicator for maintaining the developer level in the immersion tank, and said replenishing tank for supplying developer to the immersion tank as needed to maintain the developer strength.

4. The system according to claim 1, including a liquid pump and liquid filter between the liquid analyzer and immersion tank, said filter for removing impurities from the developer and the pump for circulating the developer from the immersion tank through the liquid analyzer and return, and for pumping fresh developer from the replenishing tank to the immersion tank.

5. A system for maintaining the strength of a photoresist developer fluid during the development of photoresist patterns on a semiconductor wafer, including; an immersion tank in which photoresist on the semiconductor wafers is developed, an inlet and a drain for said immersion tank, comprising a mercury-argon lamp immersed in the developer fluid, for analyzing the amount of photoresist polymer dissolved in the developer, and a control circuit for causing removal of expended developer from the immersion tank and for introducing fresh developer into said immersion tank to maintain the strength of the photoresist developer.

6. The system according to claim 5, including two valves actuated by said control circuit for removal and replenishing the developer fluid in the immersion tank.

7. The system according to claim 5 wherein said optical developer analyzer determines the amount of photoresist polymer dissolved in the developer fluid by determining the transparency of the developer fluid.

8. The system according to claim 7 wherein the developer fluid is continuously circulated through the optical developer analyzer to continuously monitor the developer fluid so as to maintain a constant strength of the developer fluid.

* * * * *